(12) United States Patent
Stainbrook et al.

(10) Patent No.: US 6,399,728 B1
(45) Date of Patent: Jun. 4, 2002

(54) STABILIZED ORGANIC PEROXYDICARBONATES COMPOSITIONS

(75) Inventors: Barbara L. Stainbrook, Collegeville; Michael S. Mendolia, Philadelphia; Terry N. Myers, Phoenixville; Peter A. Callais, Collegeville; Joseph M. Brennan, Philadelphia, all of PA (US)

(73) Assignee: ATOFINA Chemicals, Inc., Philadelphia, PA (US)

( * ) Notice: Subject to any disclaimer, the term of this patent is extended or adjusted under 35 U.S.C. 154(b) by 0 days.

(21) Appl. No.: 09/981,497

(22) Filed: Oct. 17, 2001

Related U.S. Application Data

(60) Provisional application No. 60/265,555, filed on Feb. 1, 2001.

(51) Int. Cl.$^7$ ............................. C08F 2/18; C07C 69/96
(52) U.S. Cl. ..................................... 526/230.5; 558/261
(58) Field of Search ....................... 526/230.5; 558/260, 558/261

(56) References Cited

U.S. PATENT DOCUMENTS

| | | | |
|---|---|---|---|
| 4,131,728 A | 12/1978 | Priddy | 526/204 |
| 4,178,263 A | 12/1979 | Priddy | 252/186 |
| 5,155,192 A | 10/1992 | Boelema et al. | 526/228 |
| 5,541,151 A | 7/1996 | Sanchez | 502/160 |
| 5,548,046 A | 8/1996 | Sanchez | 526/230 |
| 5,654,463 A | 8/1997 | Abma et al. | 558/261 |
| 5,654,464 A | 8/1997 | Abma et al. | 558/261 |
| 5,714,626 A | 2/1998 | Abma et al. | 558/264 |
| 5,719,304 A | 2/1998 | Frenkel et al. | 558/264 |

OTHER PUBLICATIONS

Strain et al, JACS, vol. 72, pp 1254–1263, 1950.

*Primary Examiner*—Christopher Henderson
(74) *Attorney, Agent, or Firm*—William D. Mitchell

(57) ABSTRACT

Thermally stabilized initiator composition comprising:
- (a) at least one dialkyl peroxydicarbonate, and
- (b) a stabilizing effective amount of a compound of Structure I:

I

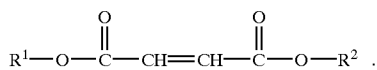

wherein $R^1$ and $R^2$ are as defined in the summary of the invention section, processes for their preparation and use are disclosed.

13 Claims, No Drawings

STABILIZED ORGANIC PEROXYDICARBONATES COMPOSITIONS

This application claims priority from provisional application No. 60/265,555, filed Feb. 1, 2001.

BACKGROUND OF THE INVENTION

This invention relates to compositions classified in the art of chemistry as dialkyl peroxydicarbonates, more specifically to new and novel thermally-stabilized initiator compositions comprising dialkyl peroxydicarbonates stabilized by the addition thereto of a stabilizing effective amount of at least one stabilizing compound selected from the group consisting of diesters of unsaturated dicarboxylic acids. The invention further relates to the use of such novel compositions as initiators of polymerization or cure of ethylenically unsaturated monomers, oligomers and polymers. The invention still further relates to the stabilization of dialkyl peroxydicarbonates during their manufacture by the inclusion of stabilizing effective amount of at least one stabilizing compound selected from the group consisting of non-hydrolyzable diesters of unsaturated dicarboxylic acids in the mixture of reactants from which a dialkyl peroxydicarbonate is to be prepared prior to, at the commencement of, or during the preparative reaction.

DESCRIPTION OF PRIOR ART

Generally, dialkyl peroxydicarbonates which are in liquid form (molten or in solution) above ca. 10. degree. c. are very hazardous owing to auto-accelerated decomposition attributed to induced decomposition of the dialkyl peroxydicarbonate.

Strain, et al. (J. Am. Chem. Soc., 1950, 72, 1254–1263) found that auto-accelerated decomposition of diisopropyl peroxydicarbonate (IPP) at room temperature could be largely suppressed by incorporating small quantities of additives such as iodine (1%) phenol (1%), hydroquinone (1%), resorcinol (1%), pyrogallol (1%), tetralin (1%), ethyl acetoacetate (1%), acetanilide (1%), trinitrobenzene (1%), 30% hydrogen peroxide (1%) and several other additives. However, when such stabilizing compositions are used to polymerize vinyl chloride monomer (VCM), there is potential for contamination of the resulting PVC resin by the additives. This contamination is undesirable, both for the PVC resin as well as for the environment. Because the thermally stabilized dialkyl peroxydicarbonate compositions of the instant invention contain olefinic unsaturation, the diluent is copolymerized with VCM at very low levels and, thus, does not contaminate the PVC resin or the effluent from the polymerization process.

U.S. Pat. No. 5,155,192 discloses stabilized peroxydicarbonate compositions containing small amounts (0.03 to 3.0 equivalent percent) of compounds containing hydroperoxy groups. Such compositions are claimed to reduce sensitivity to auto-accelerative decompositions, increase safe storage temperatures and increase self-accelerating decomposition temperatures (SADTs). However, polymer producers such as PVC producers do not like to employ initiators containing significant levels of hydroperoxides such as t-butyl hydroperoxide and cumene hydroperoxide since these impurities are free-radical chain-transfer agents and can become incorporated into the resin molecular chains as peroxy end groups. Such labile end groups can adversely affect the thermal and color stability of the resin. In addition, the lower molecular weight t-alkyl hydroperoxides such as t-butyl and t-amyl hydroperoxides are sufficiently volatile to cause problems during recycle of vinyl chloride and other monomers.

The thermally stabilized dialkyl peroxydicarbonate compositions of the instant invention, which contain compounds having olefinic unsaturation advance the peroxide art and the polymerization art since they do not cause the above resin stability problems or monomer recycle problems.

U.S. Pat. Nos. 5,541,151 and 5,548,046 disclose stabilized peroxydicarbonate solutions containing small amounts (0.05 to 1.4 equivalent percent) of compounds having an ethylenically unsaturated functional group conjugated with an acetylenic or nitrile functional group. Such compositions are stated to enhance safety for manufacture, storage, handling and use of pure liquid dialkyl peroxydicarbonates. Polymer producers, such as polyvinylchloride manufacturers prefer not to use initiators stabilized with compounds having ethylenic unsaturation conjugated with acetylenic or nitrile groups, such as acrylonitrile or methacrylonitrile due to toxicity and waste water concerns. These compounds are toxic and/or carcinogenic and would require special waste water handling and permits.

U.S. Pat. No 5,654,463 discloses the use of α-hydroxyalkyl peroxide compounds to retard the rate of decomposition of organic peroxides such as peroxydicarbonates. However, the addition of such higher half-life peroxides can cause problems during the recycle of vinyl chloride or other monomers and can cause gel formation during stripping of the resin.

U.S. Pat. No. 5,654,464 discloses the use of cyclic α-diketone compounds to retard the rate of decomposition of organic peroxides, such as peroxydicarbonates. U.S. Pat. No. 5,714,626 discloses the use of β-dicarbonyl compounds to retard the rate of decomposition of organic peroxides, such as peroxydicarbonates. U.S. Pat. No. 5,719,304 discloses the use of phosphomolybdic acid to retard the rate of decomposition of organic peroxides, such as peroxydicarbonates. However, polymer producers, including polyvinylchloride manufacturers do not like to employ peroxides stabilized using these materials since their use introduces impurities which can cause toxicity and quality problems in the final resin.

U.S. Pat. Nos. 4,131,728 and 4,178,263 disclose shock desensitized peroxide compositions which comprise a mixture of shock sensitive peroxide and a diluent. The diluent is a monomeric material containing olefinic unsaturation which does not readily homopolymerize. Peroxydicarbonates are not included in the types of peroxides which are illustrated as suitable for use in the invention of these patents. The stabilization by the various monomeric materials is for the express purpose of reducing the shock sensitivity of the peroxides being stabilized and the monomeric materials are also stated to not adversely affect the heat distortion temperatures of the final resin. There is no known correlation between the ability to reduce shock sensitivity and the ability to reduce auto-accelerated decomposition, increase safe storage temperatures or raise SADTs.

The lack of correlation can be seeing using the data in the following tables.

| Peroxide | Diluent | Time to Decomposition |
|---|---|---|
| 1,1-dimethyl-3-hydroxybutyl peroxyneodecanoate | OMS | 33 hours |
| 1,1-dimethyl-3-hydroxybutyl peroxyneodecanoate | Dibutyl Maleate | 31 hours |

-continued

| Peroxide | Diluent | Time to Decomposition |
| --- | --- | --- |
| α-cumyl peroxyneodecanoate | OMS | 27 hours |
| α-cumyl peroxyneodecanoate | Dibutyl Maleate | 22 hours |

% Assay Loss during Storage
t-Butyl Peroxyneodecanoate (75%) in OMS

|  | 0° C. | 5° C. | 10° C. |
| --- | --- | --- | --- |
| 4 weeks | 1.4 | 4.3 | 10.3 |
| 8 weeks | 3.4 | 8.9 | 19.3 |
| 12 weeks | 5.7 | 13.0 | 27.2 | t-Butyl Peroxyneodecanoate (75%) in Dibutyl Maleate

|  | 0° C. | 5° C. | 10° C. |
| --- | --- | --- | --- |
| 4 weeks | 2.0 | 3.9 | 6.5 |
| 8 weeks | 4.9 | 13.7 | 15.3 |
| 12 weeks | 12.4 | 20.2 | 30.0 |

The dibutyl maleate will have decreased the shock sensitivity as mentioned in the two aforementioned patents, but did not increase the safety characteristics of the peroxyesters. Quite unexpectedly, the safety characteristics of peroxydicarbonates are increased with the practice of the instant invention (Tables I, II, III, IV).

The above two patents also disclose that any solvent will reduce shock sensitivity but that some will also have a deleterious effect on properties of the polymer produced. Among the monomeric diluents disclosed as suitable for the invention of these patents are many that cannot be used during the manufacturing process of organic peroxides. Solid diluents may interfere with aqueous separations and many of the proposed compounds will hydrolyze under peroxide production conditions leaving pure unstabilized peroxide in the reactor at elevated temperatures; an extremely dangerous and undesirable state. Furthermore, the organic peroxides disclosed in these patents are no longer considered shock sensitive by today's standard test methods.

It is generally known to organic peroxide producers, see the Strain reference cited above, that lower molecular weight dialkyl peroxydicarbonates (such as diisopropyl peroxydicarbonate), which are in the liquid state during their production by reaction of an alkyl chloroformate with an aqueous solution of hydrogen peroxide and an inorganic base such as sodium hydroxide or potassium hydroxide, can be thermally stabilized and prevented from undergoing auto- or self-accelerating decomposition during manufacture by bubbling oxygen gas or an oxygen containing gas, e.g., air, through the reaction mixture. However, in such processes at least one settling of the reaction mixture into an upper organic phase (dialkyl peroxydicarbonate) and a lower aqueous phase is required. During these separations, agitation necessarily is terminated and bubbling of oxygen gas or an oxygen containing gas is stopped in order to enable complete separation of phases. During this quiescent period the organic dialkyl peroxydicarbonate phase is deprived of oxygen stabilizer and a hazardous self-accelerating decomposition of the liquid dialkyl peroxydicarbonate phase can occur.

This invention provides a novel manufacturing process of enhanced safety for production of liquid dialkyl peroxydicarbonates. The process employs a quantity of a diester of an unsaturated dicarboxylic acid which does not hydrolyze under the reaction conditions during manufacture, thus suppressing self-accelerating decomposition of the liquid peroxydicarbonate during manufacture and enhancing the thermal stability of the liquid dialkyl peroxydicarbonate during subsequent storage and handling.

The novel processes providing enhanced safety for the manufacture, storage, handling and use of pure liquid dialkyl peroxydicarbonates can be of the batch type, continuous type or semi-continuous type.

It should be noted that the addition of the organic hydroperoxide stabilizers for dialkyl peroxydicarbonates known in the art, such as those provided by the aforementioned U.S. Pat. No. 5,155,192, during the process for production of pure liquid dialkyl peroxydicarbonates would not be effective for thermally stabilizing the dialkyl peroxydicarbonates during processing or subsequent to processing since the art organic hydroperoxide stabilizers are reactive with alkyl chloroformates, forming OO-t-alkyl O-alkyl monoperoxycarbonates: which are not known stabilizers for dialkyl peroxydicarbonates. Furthermore, many of the organic hydroperoxides of the art are likely to partition into the aqueous phase that are involved in dialkyl peroxydicarbonate manufacturing processes, and, thus, the thermal stabilizers would not be present in the organic dialkyl peroxydicarbonate phase where thermal stabilization is needed.

Therefore, the stabilizing compounds of this invention are also superior to the stabilizers previously known for thermally stabilizing dialkyl peroxydicarbonates during production.

Definitions

As used herein and in the appended claims the following terms have the meanings here in set forth:

Substantially pure means at least about 95% pure. Stabilizing effective amount means from about 10% to about 90%, preferably about 20% to about 50% by weight, based on the weight of dialkyl peroxydicarbonate, of a compound of Structure I. In the case of stabilization of a liquid dialkyl peroxydicarbonate during its preparation, stabilizing effective amount means the above stated range of amounts of a compound of Structure I wherein $R^1$ and $R^2$ are 4 carbon atoms or greater added to the reaction calculated on the theoretical yield of dialkyl peroxydicarbonate expected from the reaction. Mixtures of stabilizing diesters of unsaturated dicarboxylic acid, such as those of Structure I may also be employed in the same total quantity proportions.

"A diester of an unsaturated dicarboxylic acid which does not hydrolyze under the reaction conditions" of preparation of alkyl peroxydicarbonate is a compound of Structure I as defined below but wherein the alkyl groups $R^1$ and $R^2$ are limited to 4 or greater carbon atoms.

SUMMARY OF INVENTION

The invention provides in a first composition aspect, a dialkyl peroxydicarbonate, containing a stabilizing effective amount of at least one compound having the Structure I:

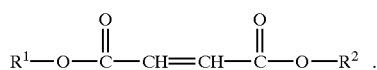

wherein $R^1$ and $R^2$ are the same or different and are selected from the group consisting of alkyl of 1 to 20 carbon atoms, cycloalkyl of 6 to 10 carbon atoms, aralkyl of 7 to 11 carbon atoms, aryl of 6 to 10 carbon atoms and mixtures thereof; and Special mention is made is made of those compounds of Structure I wherein $R^1$ and $R^2$ are selected from the above defined alkyl, cycloalkyl, aralkyl, aryl groups having 4 or more carbon atoms. Particular mention is also made of compositions of the first composition aspect of the invention wherein the dialkyl peroxydicarbonate is selected from compounds having the Structure II:

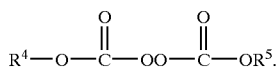

wherein $R^4$ and $R^5$ are the same or different and are selected from the group consisting of substituted or unsubstituted alkyl of 2 to 22 carbons, substituted or unsubstituted cyclcoalkyl of 5 to 12 carbons, substituted or unsubstituted bicycloalkyl of 7 to 9 carbons, and substituted or unsubstituted aralkyl of 7 to 12 carbons, with substituents for alkyl being one or more alkyl of 1 to 4 carbons, alkoxy of 1 to 6 carbons or phenoxy, substituents for cycloalkyl being one or more alkyl of 1 to 6 carbons, substituents for bicycloalkyl being one or more alkyl of 1 to 4 carbons and substituents for aralkyl being one or more alkyl of 1 to 4 carbons, chloro, bromo, methoxy and carboxy. Further mention is made of compositions wherein either or both $R^4$ and $R^5$ are selected from the group consisting of substituted or unsubstituted alkyl radicals of 2 to 22 carbons, preferably 2 to 18 carbons, more preferably 3 to 16 carbons, substituents being alkyl radicals of 1 to 4 carbons, alkoxy radicals of 1 to 6 carbons or phenoxy radicals. Further mention is also made of compositions wherein either or both of $R^4$ and $R^5$ are selected from substituted cycloalkyl radicals of 5 to 12 carbons, preferably 5 to 7 carbons, substituents being one or more alkyl radicals of 1 to 6 carbons.

The invention provides in a first process aspect, a process for polymerization of ethylenically unsaturated compounds comprising treating one or more ethylenically unsaturated compounds with an amount of at least one composition of the first composition aspect of the invention sufficient to initiate polymerization under conditions of time temperature and pressure sufficient to initiate polymerization.

Special mention is made of processes of the first process aspect of the invention wherein at least one of the unsaturated compounds to be polymerized is selected from the group consisting of an unsaturated polyester resin blend, vinyl chloride, styrene, diethylene bis(allyl carbonate), and wherein the peroxydicarbonate is selected from at least one compound having Structure II.

The invention provides in a second process aspect, a process for preparing a thermally-stabilized initiator composition of the first composition aspect of the invention which comprises reacting at least one alkyl chloroformate and aqueous hydrogen peroxide under conditions effective to form the dialkyl peroxydicarbonate in the presence of a stabilizing effective amount of at least one compound having Structure I which is a diester of an unsaturated dicarboxylic acid which does not hydrolyze under the reaction conditions.

The stabilized dialkyl peroxydicarbonate compositions of this invention, except for the presence of stabilizing amount of the aforedescribed compound of Structure I, can be in the form of a liquid containing substantially pure liquid dialkyl peroxydicarbonate, can be in the form of a solid as a substantially pure solid dialkyl peroxydicarbonate, can be in the form of a dispersion containing 10 to 50% solid dialkyl peroxydicarbonate, or can be in the form of an emulsion containing 10 to 70% liquid dialkyl peroxydicarbonate. Mixtures of dialkyl peroxydicarbonates prepared by simultaneous reaction of two or more chloroformates with aqueous hydrogen peroxide are specifically contemplated by the invention.

DETAILED DESCRIPTION OF THE PREFERRED EMBODIMENTS

A. List of Illustrative Examples

1. Components

Non-limiting examples of suitable dialkyl peroxydicarbonates that are useful for preparing the thermally stabilized dialkyl peroxydicarbonate compositions of this invention include liquid dialkyl peroxydicarbonates [melting point (mp) below 15° C.], such as diethyl peroxydicarbonate, di-n-propyl peroxydicarbonate, diisopropyl peroxydicarbonate (mp=10° C.), di-n-butyl peroxydicarbonate, diisobutyl peroxydicarbonate, di-n-hexyl peroxydicarbonate, di(2-ethylhexyl)peroxydicarbonate and di(2-methoxypropyl) peroxydicarbonate, and solid dialkyl peroxydicarbonates (mp above 15° C.), such as di(n-tridecyl)peroxydicarbonate (mp=43°–45° C.) di(n-hexadecyl)peroxydicarbonate (mp=52° C.), dibenzyl peroxydicarbonate (mp=101–102° C.), dicyclohexyl peroxydicarbonate (mp=46° C.), di(cis-3,3,5-trimethylcyclohexyl) peroxydicarbonate (mp=81°–82° C.), di(4-t-butylcyclohexyl)peroxydicarbonate (mp=91°–92° C.), dibornyl peroxydicarbonate (mp=94°–96° C.) and di(2-phenoxyethyl)peroxydicarbonate (mp=97°–100° C).

The stabilizing compounds are diesters of unsaturated dicarboxylic acids. While the compounds of Structure I and claimed herein are typical, the invention specifically contemplates as a full equivalent any compound having ethylenic unsaturation conjugated with carboxylic ester functions in the α position and which is miscible with the dialkyl peroxydicarbonate being stabilized in concentrations capable of providing an equivalent quantity of the conjugated unsaturated conjugated carboxylic ester system to that provided by the compounds of Structure I when those latter compounds are used in their contemplated concentrations. Non-limiting examples of suitable diesters of unsaturated dicarboxylic acids of Structure I that are useful for thermally stabilizing and preparing the thermally stabilized dialkyl peroxydicarbonate compositions of this invention include dibutyl maleate, dibutyl fumarate, diphenyl maleate, diethyl maleate, dimethyl maleate, di(3-methylphenyl)maleate, dioctyl maleate, dibenzyl maleate, dicyclohexyl maleate, di-t-butyl maleate, di-t-amyl maleate. Other compounds falling within the general category are well known in the literature and are readily prepared by methods well known to those skill in the art.

Non-limiting examples of suitable solvents that may optionally be used for preparing the thermally stabilized dialkyl peroxydicarbonate solutions of this invention include odorless mineral spirits (OMS), toluene, dimethyl phthalate, dibutyl phthalate and dioctyl phthalate.

2. Manufacturing Processes

This invention also provides a novel manufacturing process of enhanced safety for production of dialkyl peroxydicarbonates and simultaneously provides an alternate means for producing novel, stabilized dialkyl peroxydicarbonate compositions containing an amount of stabilizing compound sufficient to stabilize the dialkyl peroxydicarbonate that is from about 10 to about 90%, preferably 20 to 50% by weight on dialkyl peroxydicarbonate, of a compound of Structure I which will not hydrolyze under the reaction conditions.

The process employs a quantity (10 to 90%, preferably 20 to 50% by weight based on dialkyl peroxydicarbonate) of a compound of Structure I which will not hydrolyze under the reaction conditions during the processing for enhancing the thermal stability of the dialkyl peroxydicarbonate during manufacture, thus suppressing self-accelerating decomposition of the dialkyl peroxydicarbonate during subsequent storage and handling.

The novel manufacturing process for production of dialkyl peroxydicarbonates involves the following process steps:

a. Reaction Step—A substantially pure alkyl chloroformate, or a mixture of substantially pure alkyl chloroformates, (1.8 to 2.2 moles, preferably 1.9 to 2.1 moles per mole of hydrogen peroxide) is rapidly reacted with an aqueous solution of hydrogen peroxide (1.0 mole per mole of hydrogen peroxide) and sodium hydroxide or potassium hydroxide (1.9 to 2.6, preferably 2.0 to 2.2 moles per mole of hydrogen peroxide) at about −10° C. to 30° C., preferably 0° C. to 20° C., and the reaction mass is agitated for about 15–60 minutes, preferably 20–40 minutes, at 0° C. to 30° C. preferably 0° C. to 20° C.

b. Initial organic Phase/Aqueous Phase Separation—Agitation is stopped and the reaction mass is allowed to separate into an upper organic layer and a lower aqueous layer at 0° C. to 25° C., preferably 5° C. to 20° C., over a period of 5–40 minutes, preferably 10–30 minutes. The aqueous layer is drawn off and discarded.

c. Aqueous Wash and Separation—To the crude dialkyl peroxydicarbonate from step b is added a saturated aqueous salt solution (i.e., a saturated salt solution derived from ammonium, sodium and potassium chlorides, sulfates and phosphates, preferably sodium chloride) at 0° C. to 25° C., preferably 5° C. to 20° C., and the mixture is agitated for about 1–30 minutes at 0° C. to 25° C., preferably 5° C. to 20° C. Agitation is stopped and the reaction mass is allowed to separate into an upper organic layer and a lower aqueous layer at 0° C. to 25° C., preferably 5° C. to 20° C., over a period of 5–40 minutes, preferably 10–30 minutes. The aqueous layer is drawn off and discarded. This salt wash can be repeated or a different wash treatment can be employed if required, to purify the dialkyl peroxydicarbonate.

d. Drying Step—The wet dialkyl peroxydicarbonate from step c is dried over about 1–10%, preferably 5%, by weight of anhydrous sodium sulfate or anhydrous magnesium sulfate at 0° C. to 25° C., preferably 0° C. to 15° C., and the spent desiccant is separated by filtration or centrifugation at 0° C. to 25° C., preferably 0° C. to 15° C., or the wet dialkyl peroxydicarbonate is blown with a relatively dry gas (e.g., dry air) at 0° C. to 25° C., preferably 0° C. to 15° C. Then the dry peroxide is packed out and chilled prior to storage at about −25° C. to −5° C.

The addition of a compound of Structure I which will not hydrolyze under the reaction conditions in the process can be made at any of the several steps of the process. Preferably, the addition of the appropriate compound of Structure I is made shortly before the initial organic phase/aqueous phase separation step [i.e., at the end of Step a] and agitation is continued for 1–5 minutes at 0° C. to 30° C. At this stage of the process, the appropriate stabilizing compound of Structure I (thermal stabilizer) is present in the organic phase that would otherwise contain substantially pure dialkyl peroxydicarbonate. The thermal stabilizer will remain present in the substantially pure dialkyl peroxydicarbonate phase in the subsequent steps of the process, and during storage and handling. Addition of $C_1$ to $C_3$ alkyl diesters, such as those included in Structure I, at the beginning of the reaction stage [i.e., at the beginning of Step a] could result in some loss of thermal stabilizing activity owing to at least partial hydrolysis of the active diester to an inactive unsaturated mono ester or dicarboxylic acid which will be extracted into the aqueous phase.

The novel processes for pure dialkyl peroxydicarbonates can be of the batch type, continuous type or semi-continuous type:

Batch Processes—For economic commercial batch processes, large reactors, agitators and cooling capacities are required, the size of each being determined by the size of the maximum reaction mass encountered during the process and the maximum heat load required during the process. Large quantities of the product are present in crude or pure form during or at the end of the batch process. Large quantities of product are produced discontinuously at various points in time. Typical batch processes for dialkyl peroxydicarbonates are described in the chemical literature (see, for example, the Strain reference cited above).

Continuous Processes—For economic commercial continuous processes, relatively small reactors, agitators and cooling capacities are sufficient as small quantities of reactants, and wash treatments are continuously added at various stages of the process and small quantities of product are produced continuously.

Once a continuous process has been established, addition of reactants and wash treatments at different points in the process and production of product are not only continuous but also simultaneous. Continuous processes are inherently safer than batch processes for production of explosively hazardous products such as organic peroxides. A continuous process for production of pure liquid dialkyl peroxydicarbonates is described in U.S. Pat. No. 3,950,375.

Semi-Continuous Processes—these processes are hybrids of batch and continuous processes, using batch processing at stages of the process where advantageous. Generally, small reactors, agitators and cooling capacities are employed at various continuous stages of the semi-continuous processes. Larger reactors, agitators and cooling capacities are required during the batch stages of the processes. Semi-continuous processes for production of organic peroxides are generally less hazardous than batch processes.

It should be noted that addition of organic hydroperoxide stabilizers (as described in the previously referenced U.S. Pat. No. 5,155,192) for dialkyl peroxydicarbonates during the process for production of pure dialkyl peroxydicarbonates can not be done during processing since such organic hydroperoxide stabilizers are reactive with alkyl chloroformates, forming OO-t-alkyl O-alkyl monoperoxycarbonates, which are not known stabilizers for dialkyl peroxydicarbonates. Furthermore, many of the organic hydroperoxides are likely to partition into the aqueous phases that are involved in dialkyl peroxydicarbonate processes, and, thus would not be present in the organic dialkyl peroxydicarbonate phase where thermal stabilization is needed. Therefore, the diesters of unsaturated dicarboxylic acids of Structure I, of this invention are superior to the art thermal stabilizers for thermally stabilizing dialkyl peroxydicarbonates during manufacture.

3. Compositions

Non-limiting examples of the novel, thermally stabilized dialkyl peroxydicarbonate compositions of this invention, in addition to those of the examples, include those given in Table A.

TABLE A

Novel Thermally - Stabilized Dialkyl Peroxydicarbonate Compositions

| Thermal Stabilizer (Structure I) (Level, % by weight) | Peroxydicarbonate (identified by $R^4$ and $R^5$) (Level, % by weight) | Other Components (Level % by weight) |
|---|---|---|
| Dibutyl maleate (25) | Diethyl, Substantially Pure, (rest) | None |
| Dibutyl maleate (25) | Di-n-propyl Substantially Pure, (rest) | None |
| Dibutyl maleate (25) | Diisobutyl Substantially Pure (rest) | None |
| Dibutyl maleate (25) | Di-n-butyl Substantially Pure (rest) | None |
| Diethyl maleate (25) | Diisobutyl Substantially Pure (rest) | None |
| Diethyl maleate (25) | Di-(2-ethylhexyl) Substantially Pure (rest) | None |
| Diphenyl maleate (25) | Di-n-butyl Substantially Pure (rest) | None |
| Di-sec-butyl fumarate (25) | Di-n-hexyl Substantially Pure (rest) | None |
| Dioctyl maleate (25) | Di-(2-methoxypropyl) Substantially Pure (rest) | None |
| Dioctyl maleate (25) | Di-n-propyl Substantially Pure (rest) | None |
| Dioctyl maleate (25) | Di-(2-phenoxy ethyl) Substantially Pure (rest) | None |
| Diphenylmaleate (25) | Di-(4-t-butylcyclohexyl) Substantially Pure (rest) | None |
| Dioctyl maleate (15) | Di-sec-butyl (75) | Odorless Mineral Spirits (rest) |
| Di-n-butyl maleate (20) | Di-n-propyl (60) | Odorless Mineral Spirits (rest) |
| Dibutyl maleate (15) | Di(2-ethylhexyl) (60) | Odorless Mineral Spirits (rest) |
| Diethyl maleate (15) | Di-isopropyl (75) | Odorless Mineral Spirits (rest) |
| Dihexyl maleate (10) | Di-sec butyl (60) | Odorless Mineral Spirits (rest) |
| Dihexyl maleate (5) | Di(2-ethylhexyl) (75) | Di-butyl phthalate (rest) |

B. Utility

1. Polymerization of Ethylenically Unsaturated Monomers

In the free-radical polymerizations of ethylenically unsaturated monomers at suitable temperatures and pressures the novel stabilized peroxydicarbonate initiator compositions of this invention were found to be effective initiators with respect to efficiency (initiator requirements, etc.). Ethylenically unsaturated monomers include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3 butadiene, isoprene and chloroprene; vinyl esters, such as vinyl acetate, vinyl propionate, vinyl laurate, vinyl benzoate and divinyl carbonate; unsaturated nitriles, such as acrylonitrile and methacryclonitrile; acrylic acid and methacrylic acid and their anhydrides, esters and amides, such as acrylic acid anhydride, allyl, methyl, ethyl, n-butyl, 2-hydroxyethyl, glycidyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride, perhalo olefins, such as tetrafluoroethylene, hexafluoropropylene and chlorotrifluoroethylene; vinyl ethers, such as methyl vinyl ether, ethyl vinyl ether and n-butyl vinyl ether, allyl esters, such as allyl acetate, allyl benzoate, allyl ethyl carbonate, triallyl phosphate, diallyl phthalate, diallyl fumarate, diallyl glutarate, diallyl adipate, diallyl carbonate, diethylene glycol bis(allyl carbonate) (i.e., ADC); acrolein; methyl vinyl ketone; or mixtures thereof.

Temperatures of 25° C. to 100° C., preferably 30° C. to 90° C., more preferably 75° C. and levels of novel stabilized peroxydicarbonate initiator compositions (on a pure basis) of 0.002 to 3%, preferably 0.005% to 1%, more preferably 0.01% to 0.75% by weight based on monomer (amount effective for initiation), are normally employed in conventional polymerizations and copolymerizations of ethylenically unsaturated monomers. One of skill in art will recognize that some of the above listed monomers will undergo polymerization at still lower temperatures in the presence of the peroxydicarbonates contemplated by this invention and that certain monomers, such as ethylene are conventionally polymerized at pressures greater than atmospheric. The processes contemplated by this invention include such conventional processing conditions. The novel stabilized peroxydicarbonate compositions of this invention can be used in combination with other free-radical initiators such as those disclosed at the bottom of column 4 and the top of column 5 of U.S. Pat. No. 4,525,308. Using the peroxide compositions of this invention in combination with these initiators adds flexibility to the processes of polymer producers and permits them to "fine tune" their polymerization processes.

Use of the stabilized percarbonates of this invention in polymerization of vinyl chloride provides polyvinyl chloride suitable for food contact usage.

Polyvinylchloride (PVC) polymer is used as the polymeric component of a wide variety of useful articles such as shoes, tablecloths, wall coverings, floor tiles, phonograph records, upholstery, pipe, house siding and packaging. PVC of itself is virtually unprocessable. It must be compounded with a wide array of additives and modifiers so that it may be thermoformed by molding, extrusion, calendaring and casting. Additives and modifiers include lubricants plasticizers, antistats, pigments, filters, impact modifiers, polymeric process aids and thermal stabilizers.

One class of PVC and PVC-based compounds is that intended for food contact application. These usually take the form of plasticized flexible films for meat wraps, rigid film for candy wrap, rigid clear bottles for oil and aqueous foods, thermoformed packaging for foods and pharmaceuticals and piping systems for potable water. In order to meet the stringent specifications for PVC and PVC compounds intended for food contact applications, it is required that all materials used in the manufacture of the PVC polymer or incorporated as additives or modifiers be of adequate safety for their intended use. Thus, the additives and process aids must be of sufficient low toxicity that they do not present a problem, or they may be essentially non-extractable from the finished article, and therefore, do not become food additives requiring specific regulations. In addition, the polymerization catalyst must at a minimum not leave residues in the resin which are toxic or which exceed regulatory permitted limits.

Within the scope of the present invention, specific organic peroxide polymerization catalyst compositions comprising dialkyl peroxydicarbonate and specific dialkyl ethylenically unsaturated dicarboxylic acid esters are preferred polymerization catalysts for polymerization of food contact PVC and PVC compounds. Most preferred are compositions comprising dialkyl esters of maleic acid in which the alkyl groups consist of $C_4$ or greater. As stated above, dialkyl esters of maleic acid of less than $C_4$ tend to be hydrolytically unstable during the manufacture of the peroxide, but may be added to the peroxide itself as stabilizers.

As stated above, the principal function of the dialkyl ethylenically unsaturated dicarboxylic acid ester in the organic peroxide mixture is to stabilize the organic peroxide against degradation. In this respect, the integrity and catalytic strength of the organic peroxide is preserved and PVC of greater purity is produced when such stabilized catalyst compositions are employed in its manufacture. This is particularly important in the production of PVC intended for food application in order to minimize extractables. It is believed that the extraction of the stabilizing portion of the food-grade polymerization catalyst mixture is reduced, in part, through copolymerization of the ethylenically unsaturated dicarboxylic acid moiety with vinyl chloride monomers during the manufacture of PVC so that they are incorporated in low concentration into the PVC polymer chain and are, thus, not extractable.

It is important in the preparation of PVC compounds intended for food contact application that undesirable extractable residues from reaction of polymerization catalysts and polymerization catalyst stabilizers be avoided.

2. Curing of Unsaturated Polyester Resins

In the curing of unsaturated resin compositions (which are also ethylenically unsaturated compounds) by heating at suitable curing temperatures in the presence of free-radical curing agents, the novel stabilized peroxydicarbonate initiator compositions of this invention exhibit enhanced curing activity in the curable unsaturated polyester resin compositions. Unsaturated polyester resins that can be cured by the novel thermally stabilized dialkyl peroxydicarbonate compositions of this invention usually include an unsaturated polyester and one or more ethylenically unsaturated monomers.

The unsaturated polyesters are, for instance, polyesters as they are obtained by esterfying at least one ethylenically unsaturated di- or polycarboxylic acid, anhydride or acid halide, such as maleic acid, allylmalonic acid, tetrahydrophthalic acid, and others, with saturated and unsaturated di- or polyols, such as ethylene glycol, diethylene glycol, triethylene glycol. 1,2-and 1,3 -propanediols, 1,2-, 1,3- and 1,4-butanediols, 2,2-dimethyl-1,3 propanediol, 2-hydroxymethyl-2-methyl-1,3-propanediol, 2-buten-1,4-diol, 2-butyn-1,4-diol, 2,4, 4-trimethyl-1,3-pentanediol, glycerol, pentaerythritol, mannitol and others. Mixtures of such di- or polycarboxylic acids may be partially replaced by saturated di- or polycarboxylic acids, such as adipic acid, succinic acid, sebacic acid and other, and/or by aromatic di- or polycarboxylic acids, such as phthalic acid, trimellitic acid, pyromellitic acid, isophthalic acid. The acids used may be substituted by groups such as halogen. Examples of such suitable halogenated acids are, for instance, tetrachlorophthalic acid, tetrabromophthalic acid, 5,6-dicarboxy-1,2, 3,4,7,7-hexachlorobicyclo(2.2.1)-hept-2-ene and others.

The other component of the unsaturated polyester resin composition, the polymerizable monomer or monomers, can preferably be ethylenically unsaturated monomers, such as styrene, α-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl methacrylate, ethyl acrylate, and others, or mixtures thereof, which are copolymerizable with said unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid) as well as the monomer component, styrene.

Other types of unsaturated polyester resin compositions can be cured using the novel stabilized peroxydicarbonate initiator compositions of this invention as curing catalysts. These resins, called unsaturated vinyl ester resins, consist of a vinyl ester resin portion and one or more polymerizable monomer components.

The vinyl ester resin component can be made by reacting a chloroepoxide, such as epichlorohydrin, with appropriate amounts of a bisphenol such as Bisphenol A [2,2-(4-hydroxyphenyl)propane], in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to 200° C. and levels (amounts sufficient to initiate polymerization or cure) of novel stabilized peroxydicarbonate initiator compositions of about 0.05% to 5% or more, preferably 0.10% to 4%, more preferably 0.25% to 3% by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

3. Curing of Allyl Diglycol Carbonate (ADC) Resins

In the curing or polymerizing of diethylene glycol bis (allyl carbonate) (ADC), $CH_2$=$CHCH_2$—O—C(=O)—O—$CH_2CH_2$—O—$CH_2CH_2$—O—(=O)—O—$CH_2CH$=$CH_2$, by heating ADC monomer at suitable curing temperatures in the presence of free-radical curing agents, the novel stabilized peroxydicarbonate initiator compositions of this invention exhibit enhanced curing or polymerizing activity for ADC monomer compositions. ADC was introduced commercially as CR-39™ monomer (CAS REG. No. 142-22-3) by Pittsburgh Plate Glass Company (PPG) and is produced by reacting diethylene glycol bis (chloroformate) with allyl alcohol in the presence of alkali (R. Dowbenko, in J. I. Kroschwitz and M. Howe-Grant, eds., Kirk-Othmer—Encyclopedia of Chemical Technology, "Allyl Monomers and Polymers," Fourth Edition, Vol. 2, Wiley-Interscience Publication, John Wiley & Sons, Inc., New York, 1992 pp 163–168). ADC monomer can cured or polymerized alone, or with other comonomers such as acrylic acid esters, methacrylic acid esters, allyl esters, diallyl dicarboxylates (e.g., diallyl phthalate), maleic anhydride and other monomers to produce clear castings or lenses that are transparent, tough, break-resistant and solvent-resistant. Curing or polymerizing of ADC monomer compositions are carried out in bulk (no solvent present). In general, curing or polymerizing of ADC monomer compositions to form cast sheets or lenses is carried out in two stages. The first stage involves the major part of the polymerization and occurs in the presence of the curing initiator, usually a lower dialkyl peroxydicarbonate, at temperatures of 35° C. to 120° C. Curing or polymerization times vary from about 5 hours to 50 hours. Generally a time-temperature profile is employed in the first stage. An example of a time-temperature profile given below:

| TYPICAL CURE TEMPERATURE SCHEDULE FOR CURING OF ADC | |
|---|---|
| TIME (HOURS) | TEMPERATURE (° C.) |
| 0.0 | 61 |
| 1.0 | 62 |
| 3.0 | 64 |
| 7.0 | 68 |
| 8.0 | 69 |
| 8.5 | 74 |
| 9.0 | 79 |
| 9.5 | 86.5 |
| 10.0 | 96.5 |
| 10.5 | 115 |
| 10.75 | 85 |
| 11.0 | 65 |
| 11.25 | 40 |
| 11.5 | 30 |

The second stage of the curing or polymerizing of ADC monomer compositions involves post-curing or annealing of the ADC resin for one to several hours at 100° C. to 150° C. An example of post-curing of the ADC resin would be 2 hours at 115° C.

Levels (amounts sufficient to initiate polymerization or cure) of novel stabilized peroxydicarbonate initiator compositions of about 1% to 6% or more, preferably 2% to 5% more preferably 2.5% to 4% by weight of curable or polymerizable ADC monomer composition are normally employed.

The ADC resin compositions described above can be filled with various materials, such as antioxidants (AO's), heat, ultraviolet (UV) and light stabilizers, tints, photochromic additives and dyes. In addition, the ADC resin compositions can contain additives such as acrylic polymers and the anti-shrink, low molecular weight acrylic resins disclosed in U.S. Pat. No. 4,217,433. Such anti-shrink additives are employed to counter the 14% shrinkage that occurs when ADC monomer is polymerized.

In all cases the time, temperature and pressure conditions employed in any polymerization are not contemplated as critical by the invention and conditions normally employed by those of skill in the art may be similarly employed in the processes of this invention.

C. Preparative Methods

Preparations of Novel Stabilized Peroxydicarbonate Compositions

The dialkyl peroxydicarbonate portion of the novel, thermally stabilized peroxydicarbonate initiator compositions of this invention can be prepared by methods well known in the art (F. Strain, et al., J. Am, Chem. Soc., 1950, 72, 1254–1263, and U.S. Pat. No. 3,950,375).

The compounds of Structure I are known compounds and are commercially available or may be prepared by synthetic methods well known to a skilled chemist.

The novel, stabilized peroxydicarbonate initiator compositions may also be prepared by thoroughly mixing 10 to 90%, preferably 20 to 50% by weight based on weight of the dialkyl peroxydicarbonate, of a diester of an unsaturated dicarboxylic acid of Structure I with said dialkyl peroxydicarbonate at −20° C. to 20° C.

The following examples are presented to further illustrate the best mode contemplated for the practice of the invention and to provide detailed preparative illustrations and are not intended to limit the scope of the present invention.

EXAMPLE 1

Time to Decomposition Tests a). Sample Preparation

Samples of pure peroxydicarbonate and the respective diluent were prepared by stirring the diluent into the liquid peroxydicarbonate at 0° C. until complete solution was attained (usually 1–2 minutes). The solutions were placed in a freezer and allowed to equilibrate to −10° C.

b). Time to Decomposition

An equilibrated 150 gram sample was placed in a 500 ml Dewar flask equipped with a foam lid and thermocouple. The sample was allowed to warm. Decomposition was characterized by rapid decomposition at the liquid surface accompanied by rapid expulsion of decomposition products from the dewar orifice. Once decomposition started, the contents of the dewar were consumed in 10 seconds or less. The time required for onset of decomposition was noted. In the case of pure di(2-ethylhexyl)peroxydicarbonate containing no diluent, rapid decomposition occurred after 7 hours. Thermally stabilizing diluents significantly increased the time required for the onset of rapid decomposition. An inert diluent such as odorless mineral spirits (OMS) (25% by weight) only increased the time of decomposition to 24 hours. Table I tabulates the diluent used, the diluent level and the time to decomposition for the 150 g samples of the peroxydicarbonate compositions listed containing various additives.

TABLE I

| Peroxide | Diluent | Stabilizer | Time to Decomposition |
|---|---|---|---|
| Di(2-ethylhexyl) Peroxydicarbonate | none | none | 7 hours |
| Di(2-ethylhexyl) Peroxydicarbonate | OMS (25%) | none | 24 hours |
| Di(2-ethylhexyl) Peroxydicarbonate | OMS (25%) | t-butyl hydroperoxide (0.2%) | 35 hours |
| Di(2-ethylhexyl) Peroxydicarbonate | Dibutyl Maleate (25%) | none | 35 hours |
| Di(sec-butyl) Peroxydicarbonate | OMS (40%) | none | 16 hours |
| Di(sec-butyl) Peroxydicarbonate | Dibutyl Maleate (40%) | none | 31 hours |

The results in Table I show that diluents such as OMS and dibutyl maleate increased the decomposition time for pure di(2-ethylhexyl)peroxydicarbonate and di(sec-butyl) peroxydicarbonate in the time to decomposition test. However, the most effective thermal stabilizing diluents, as judged by significantly increased time to decomposition test time were the thermal stabilizing diluents of this invention according to Structure I.

EXAMPLE 2

Thermal Stability Losses For Di(2-ethylhexyl) peroxydicarbonate

Samples of pure di(2-ethylhexyl)peroxydicarbonate (LUPEROX® 223), manufactured by Elf Atochem North America, Inc.) containing the diluents shown were thermal stability tested in a bath held at the temperatures shown for the time shown in Table II. The normal recommended storage temperature for LUPEROX 223 is −18° C. (0° F.), therefore, the dialkyl peroxydicarbonate samples, with and without additives, were stability tested for a loss of active oxygen at a temperature significantly above the normal, recommended storage temperature. The results of this stability testing are summarized in Table II.

Most unexpected is the increase in the storage stability. At higher temperatures, less assay loss occurs with the diluent of the present invention than with other diluents or stabilized products.

The compounds of Structure I clearly gave superior stability to the standard OMS diluent and the OMS diluent/ t-butyl hydroperoxide mixture.

TABLE IV

| Peroxide | Solvent | 3 day loss 10° C. | 3 day loss 15° C. | 3 day loss 20° C. |
|---|---|---|---|---|
| Di(2-ethylhexyl) peroxydicarbonate | OMS (25%) | 1.7% | 13.7% | 63.4% |

TABLE II

| Peroxide | Diluent | Stabilizer | 4 wk loss 5° C. | 4 wk loss 10° C. | 8 wk loss 5° C. | 8 wk loss 10° C. | 12 wk loss 5° C. | 12 wk loss 10° C. |
|---|---|---|---|---|---|---|---|---|
| Di(2-ethylhexyl) peroxydicarbonate | OMS | none | 5.7% | 67.8% | 42.7% | 88.9% | 72.9% | 94.0% |
| Di(2-ethylhexyl) peroxydicarbonate | OMS | t-butyl hydroperoxide | 4.8% | 55.4% | 23.9% | 86.9% | 66.2% | 93.2% |
| Di(2-ethylhexyl) peroxydicarbonate | Dibutyl Maleate | none | 4.4% | 14.0% | 9.1% | 26.9% | 15.2% | 36.5% |

EXAMPLE 3

Self-Accelerating Decomposition Temperature (SADT) Test for Di(2-ethylhexyl)Peroxydicarbonate Containing the Diluents Shown in Table III The Self-Accelerating Decomposition Temperature (SADT) Test is used by organic peroxide producers to determine the lowest temperature at which an organic peroxide composition, in its largest commercial package, will undergo a self-accelerating decomposition in one week (Suggested Relative Hazard Classification of Organic Peroxides, Organic Peroxide Producers Safety Division, The Society of the Plastics Industry, Inc., New York, pp. 17–20, 1992). The SADT test also evaluates the severity of the decomposition that occurs at the SADT temperature. The test is thoroughly described in the technical literature by the Organic Peroxide Producers Safety Division (OPPSD).

SADT tests were carried out on 8 pound packages (1 gallon) of pure di(2-ethylhexyl)peroxydicarbonate (LUPEROX 223), with and without the diluents shown. The SADT results obtained are summarized in Table III.

TABLE III

| Peroxide | Diluent | Stabilizer | SADT |
|---|---|---|---|
| Di(2-ethylhexyl) Peroxydicarbonate | none | none | 10° C. |
| Di(2-ethylhexyl) Peroxydicarbonate | OMS (25%) | none | 15° C. |
| Di(2-ethylhexyl) Peroxydicarbonate | OMS (25%) | t-butyl hydroperoxide (0.2%) | 20° C. |
| Di(2-ethylhexyl) Peroxydicarbonate | Dibutyl Maleate (25%) | none | 25° C. |

EXAMPLE 4

Additional Thermal Stability Loss Tests for Dialkyl Peroxydicarbonates

Samples of the dialkyl peroxydicarbonates listed in Table IV diluted with the diluents shown in the Table were tested analogously to the test in Example 2 and the 3 day losses at 10° C., 15° C. and 20° C. were measured.

TABLE IV-continued

| Peroxide | Solvent | 3 day loss 10° C. | 3 day loss 15° C. | 3 day loss 20° C. |
|---|---|---|---|---|
| Di(2-ethylhexyl) peroxydicarbonate | OMS/t-butyl hydroperoxide (25%/0.2%) | 1.7% | 4.5% | 32.2% |
| Di(2-ethylhexyl) peroxydicarbonate | Dibutyl maleate (25%) | 1.0% | 3.2% | 11.7% |
| Di(2-ethylhexyl) peroxydicarbonate | Di-sec-butyl Fumarate (25%) | 1.2% | 3.8% | 17.9% |
| Di(2-ethylhexyl) peroxydicarbonate | Dioctyl Maleate (25%) | 1.4% | 4.1% | 10.1% |
| Di(sec-butyl) peroxydicarbonate | OMS (25%) | 10.8% | 26.0% | 49.9% |
| Di(sec-butyl) peroxydicarbonate | Dioctyl Maleate (25%) | 0.0% | 1.0% | 6.2% |

EXAMPLE 5

Comparison of Vinyl Chloride Suspension Polymerization Efficiency using Di-(2-ethylhexyl) peroxydicarbonate (LUPEROX 223) and α-Cumyl peroxyneodecanoate (LUPEROX 188), a Standard Low Temperature PVC Initiator Using Standard Diluents and a Typical Diluent of Structure I and of the Resulting Resin Properties Vinyl chloride suspension polymerizations were carried out at 58° C. in order to determine the effect of initiators stabilized according to the present invention and stabilized conventionally on conversion of vinyl chloride monomer (VCM) to poly(vinyl chloride) PVC).

The following recipe was employed in these vinyl chloride polymerizations:

| Ingredient | Parts by weight |
| --- | --- |
| Vinyl Chloride Monomer | 100 |
| Water (deionized) | 200 |
| Polyvinyl Alcohol* (Alcotex ® 72.5) | 0.6 |
| Polyvinyl Alcohol* (Alcotex ® 55-002) | 0.2 |
|  | as detailed below and in the following Tables |

*Polyvinyl Alcohol, manufactured by Harlow Chemical Company, Ltd.

Polymerization Procedure

The polymerization vessel employed in the vinyl chloride suspension polymerizations was equipped with a pressure gauge, mechanical stirrer, cooling coils and thermocouples for various temperatures measurements. Water and the polyvinyl alcohols were added to the vessel. The vessel was submerged in a water bath to maintain temperature. Once the contents reached the polymerization temperature of 58° C., the required amount of vinyl chloride monomer and 0.001% by weight of initiator samples was added to the vessel. The time to pressure drop was measured and taken as the end of the polymerization reaction. The times to pressure drop are shown in Table V.

The resin was isolated and purified by standard means and the resin properties determined. Dioctyl phthalate porosity and Powder Mix Times are shown in Table VI. Dioctyl phthalate porosity test is based on ASTM Method D3367. Powder Mix Time test is based on ASTM Method D2396. Material was compounded and processed into tensile bars and tested according to ASTM Method D-638-99 Type 4 testing. Tensile test results are shown in Table VII. Samples of resin were also compounded and made into cubes and tested using a Metrastat® instrument (manufactured by Metrastat S.A.). The samples were exposed to 207° C. for a thirty minute cycle. The compounded samples were essentially identical in performance in this procedure.

TABLE V

Polymerization Results

| Diluent of Luperox 188 | Diluent of Luperox 223 | Time to pressure drop |
| --- | --- | --- |
| OMS* | OMS | 3 hour 25 min |
| OMS | Dibutyl maleate | 3 hour 36 min |
| Dibutyl maleate | OMS | 3 hour 38 min |
| Dibutyl maleate | Dibutyl maleate | 3 hour 28 min |

*OMS = odorless mineral spirits

TABLE VI

Resin Properties

Dioctyl Phthalate (DOP) Porosity

-Porosity of the PVC particles based on DOP absorption
-0.354 (dibutyl maleate) versus 0.369 (OMS) - no difference Powder Mix Time -The time required for all ingredients to be absorbed into the PVC
-378 sec (dibutyl maleate) versus 402 sec (OMS) - no difference

TABLE VII

Tensile Test Results

| Resin | Stress at maximum (psi) | Strain at maximum (%) |
| --- | --- | --- |
| Dibutyl maleate | 2380 ± 25.2 | 360 ± 9.3 |
| OMS Diluent | 2390 ± 43.9 | 330 ± 31 |

It will be apparent to one of skill in the art that and the invention contemplates that in addition to maleic and fumaric acids specifically mentioned and claimed, butenedioic acids substituted with alkyl groups in the two position, such as, dibutyl citraconate, dipropyl 2-(isopropyl)-1,4-but-2-endioate, dibutyl 2-ethyl-2-buten-1,4-dioate as well as their higher alkyl analogues will be full equivalents as stabilizers for peroxydicarbonates and in their use to initiate the polymerization of vinyl chloride to provide the same high quality polyvinyl chloride as the maleic and fumaric esters of Structure I.

The subject matter which applicant regards as his invention is particularly pointed out and distinctly claimed as follows.

We claim:

1. A composition comprising a dialkyl peroxydicarbonate containing a stabilizing effective amount of at least one compound having the Structure I,

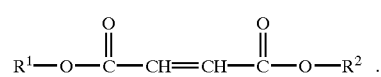

where $R^1$ and $R^2$ are the same or different and are selected from the group consisting of alkyl of 4 to 20 carbons, cycloalkyl of 6 to 10 carbons, aryl of 6 to 10 carbons, aralkyl of 7 to 11 carbons, and mixtures thereof.

2. A composition as defined in claim 1 wherein $R^1$ and $R^2$ are selected from the group consisting of alkyl of 4 to 20 carbons, carbons, and aryl of 6 to 9 carbons.

3. A composition as defined in claim 2 wherein the compound having Structure I is selected from the group consisting of di-n-butyl maleate, di-n-butyl fumarate, di-isobutyl maleate, di-t-butyl maleate, di-isobutyl fumarate, and di-t-butyl fumarate.

4. A composition as defined in claim 1 wherein the dialkyl peroxydicarbonate has the Structure II:

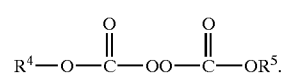

where $R^4$ and $R^5$ are the same or different and are selected from the group consisting of substituted or unsubstituted alkyl of 2 to 22 carbons, substituted or unsubstituted bicycloalkyl of 7 to 9 carbons, and substituted or unsubstituted aralkyl of 7 to 12 carbons, with substituents for alkyl being one or more alkyl of 1 to 4 carbons, alkoxy of 1 to 6 carbons, or phenoxy, substituents for cycloalkyl being one or more alkyl of 1 to 4 carbons, and substituents for aralkyl being one or more alkyl of 1 to 4 carbons, chloro, bromo, methoxy or carboxy.

5. A composition as defined in claim 4 wherein $R^4$ and $R^5$ are the same or different and are selected from the group consisting of substituted or unsubstituted alkyl and substituted or unsubstituted cycloalkyl.

6. A composition as defined in claim 5 wherein $R^4$ and $R^5$ are the same or different and are substituted or substituted alkyl of 2 to 22 carbons.

7. A composition as defined in claim 1 wherein the dialkyl peroxydicarbonate is selected from the group consisting of di-n-propyl peroxydicarbonate, diisopropyl peroxydicarbonate, di-sec-butyl peroxydicarbonate and di(2-ethylhexyl)peroxydicarbonate.

8. An improved process for the preparation of dialkyl peroxydicarbonate composition wherein at least one alkyl chloroformate is reacted with aqueous hydrogen peroxide in a reaction mixture containing aqueous base wherein the improvement comprises adding from about 10% to about 90% by weight of at least one compound of Structure I:

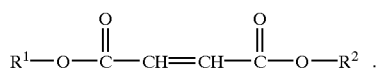

I wherein $R^1$ and $R^2$ are the same or different and are selected from the group consisting of hydrogen, alkyl of 4 to 20 carbons, cycloalkyl of 6 to 10 carbons, aryl of 6 to 10 carbons, aralkyl of 7 to 11 carbons, or mixtures thereof to said reaction mixture prior to initiation of, at the time of initiation of, at any time during the reaction between said alkylchloroformate and said aqueous hydrogen peroxide, or to the dialkyl peroxydicarbonate so formed prior to or during its purification.

9. An improved process as defined in claim 8 wherein a compound of Structure I is added to the reaction mixture at the end of the reaction between the dialkyl chloroformate and the aqueous hydrogen peroxide prior to separation of crude dialkyl peroxydicarbonate from the reaction mixture.

10. An improved process as defined in claim 8 wherein subsequent to the separation of crude dialkyl peroxydicarbonate so formed from the reaction mixture, and prior to or during purification of the dialkyl peroxydicarbonate, a compound of Structure I is added to the crude dialkyl peroxydicarbonate.

11. An improved process as defined in claim 8 wherein a compound of Structure I is added to the reaction mixture prior to or at the time of initiation the reaction between the alkyl chloroformate and the aqueous hydrogen peroxide.

12. An improved process as defined in claim 8 wherein a compound of Structure I is added to the reaction mixture during the reaction of the alkyl chloroformate and the aqueous hydrogen peroxide.

13. A process for the polymerization of vinyl chloride wherein the polyvinyl chloride so produced is suitable for food contact which comprises treating vinyl chloride with an initiating effective amount of a composition as defined in claim 1 under conditions of time, temperature and pressure sufficient to initiate and complete said polymerization of vinyl chloride.

* * * * *